United States Patent [19]

Lazzara et al.

[11] Patent Number: 4,988,297
[45] Date of Patent: Jan. 29, 1991

[54] ALIGNMENT CORRECTOR FOR DENTAL IMPLANTS

[75] Inventors: Richard J. Lazzara, Lake Worth; Keith D. Beaty, West Palm Beach, both of Fla.

[73] Assignee: Implant Innovations, Inc., West Palm Beach, Fla.

[21] Appl. No.: 162,507

[22] Filed: Mar. 1, 1988

[51] Int. Cl.$^5$ .............................................. A61C 8/00
[52] U.S. Cl. .................................... 433/173; 433/174
[58] Field of Search ................ 433/173, 174, 175, 176

[56] References Cited

U.S. PATENT DOCUMENTS

| | | | |
|---|---|---|---|
| 4,531,915 | 7/1985 | Tatum, Jr. | 433/173 |
| 4,575,340 | 3/1986 | Lustig | 433/173 |
| 4,645,453 | 2/1987 | Niznick | 433/173 |
| 4,713,004 | 12/1987 | Linkow et al. | 433/174 |
| 4,731,085 | 3/1988 | Koch | 433/173 |
| 4,738,623 | 4/1988 | Driskell | 433/173 |
| 4,758,161 | 7/1988 | Niznick | 433/173 |
| 4,780,080 | 10/1988 | Haris | 433/173 |
| 4,793,808 | 12/1988 | Kirsch | 433/173 |
| 4,826,434 | 5/1989 | Krueger | 433/174 |
| 4,832,601 | 5/1989 | Linden | 433/173 |
| 4,854,872 | 8/1989 | Detsch | 433/173 |

FOREIGN PATENT DOCUMENTS 3413811 10/1985 Fed. Rep. of Germany ... 433/174 X

*Primary Examiner*—Robert P. Swiatek
*Assistant Examiner*—Nicholas D. Lucchesi
*Attorney, Agent, or Firm*—Alfred H. Rosen

[57] ABSTRACT

An alignment corrector for a dental implant which is axially misaligned relative to a desired axis has a base member that is removably attachable to the implant with reproducible orientation around the axis of the implant and a corrector member providing a receiver to support a prosthesis on a support that is correctly aligned relative to the desired axis. The angular difference between the misaligned axis and the desired axis is fixed between the two members in a variety of structures.

4 Claims, 4 Drawing Sheets

ALIGNMENT CORRECTOR FOR DENTAL IMPLANTS

This invention relates in general to the field of prosthodontic restoration; more particularly to dental implant systems wherein an object substituting for a natural tooth root is surgically implanted in edentulous bone of the alveolar arches of the jaws, now commonly known as dental implants.

Dental implants are coming into increasingly-wide use, so much so that a new field of "implantology" is emerging, giving wider scope to the more general field of prosthodontic restoration. After one or more dental implants has or have been successfully implanted, usually by an oral surgeon, or a periodontist, in the jawbone(s) of a patient, the restorative dentist has the task of fashioning one or more prosthodontic restoration(s) and attaching it or them to the implants in a way that will provide a cosmetically attractive as well as structurally adequate dental restoration. Initial successes were based on structurally sound biocompatible implant devices realized in titanium which only recently became commercially available, and are now appearing in a variety of designs and configurations. Little or no attention was paid to cosmetic considerations, with the result that a restorative dentist seeking to provide a patient with an anatomically pleasing restoration must bring a considerable amount of personal ingenuity to the task of building the restoration, which is both expensive and time-consuming. A need exists to provide components which will enable a restorative dentist to link dental implants and prosthodontic restorations together into a structurally sound and cosmetically pleasing dental restoration. This invention addresses that need.

In a typical dental implant a titanium post is press-fitted or screwed into a hole drilled in a jawbone to receive it, and the post is left there, covered by the fleshy gum tissue until osseointegration takes place, firmly fixing the post in the jawbone. Thereafter, the gum tissue is opened to expose an end of the post, which is now available to support a prosthodontic restoration. A primary requirement of a support for dental restoration is that it shall be fixed on a desired axis. In cases where the implant is to be used together with another implant, or a root canal post or an otherwise modified natural tooth the axis of the implant must be parallel or nearly parallel to the axis or axes of the other support or supports for a bridge or a splint. In the case where only a single lost tooth is to be restored the new tooth should be axially oriented in parallel with adjacent teeth. On the other hand the surgeon or periodontist who put the implant in place was constrained by the shape and other conditions of the jawbone, for example, root of an adjacent tooth, to drilling the hole for the implant in the best location available to receive it. The hole may thus be oriented on an axis which is not the desired axis for that implant. A reliable means to change or correct the direction of the axis that will be available to the restoration is needed.

Heretofore resort has been had to bendable pins having thin neck portions, shown for example in U.S. Pat. No. 4,645,453. Such pins have been known to break in use. Cement-in pre-angled abutments have been suggested. Bendable pins made of combustible plastic make possible the casting of a metal replica of a pre-bent plastic pin. Another device for changing the axial direction of an implant uses a ball and socket joint with a clamp. This device is complicated and concentrates stress in a small neck supporting the ball.

It is highly desirable that a dental restoration supported on an implant or implants be assembled of components which can be disassembled. The opposite alternative could result in a need to destroy or damage an otherwise surgically sound implant in order to restore or replace an excessively worn or broken tooth or bridge. The bendable pins and cement-in abutments referred to above do not provide for such disassembly. Moreover such pins are limited in use, since they provide only a coping end on which to build a restoration. A wider variety of adaptable components is required.

According to the present invention a parallelism corrector device for use with a dental implant that is axially misaligned relative to a desired axis is provided in a single rigid body which is removably attachable to a dental implant. This corrector device embodies with high precision the necessary axial correction angle together with reproducible orientation around the implant axis, with the result that it establishes the desired axis correctly and accurately when first installed on the implant, and repeatedly if later removed and reinstalled.

For example, the dental implant may have an internally-threaded bore and the parallelism corrector device may have a threaded post by which to fix the corrector device to the implant; and the threads of the bore and the post may be so indexed that the post will begin to engage in the bore at only one possible angular orientation around the axis of the bore, with the result that the corrector device will be fixed to the implant with a prescribed angular orientation around that axis. If the corrector device is removed from the implant and thereafter refitted to it, the same angular orientation between the corrector device and the implant will be reproduced; it is a prescribed orientation between these two parts. In this specification and the claims appended to it the term "reproducible orientation" refers to this feature of the invention. Such an arrangement is described later in this specification with reference to FIG. 1 of the appended drawings.

Correctors according to the invention can be made to approximate the dimensions of short trans-tissue abutments that are now in use where no axis correction is needed. Thus, according to the invention, a prosthodontist has available an axis-corrector trans-tissue abutment which when used can change a complicated case into a relatively simple case as though the implant or implants were all fixed in the jawbone parallel to the desired axis.

Generally according to the invention, the difference between a misaligned axis and the desired axis is determined, this angular difference is fixed between a member that is adapted for fixation to the implant on the misaligned axis and a member which is intended for support of a prosthesis on the desired axis, and the two members are joined together rigidly.

Correctors according to the invention, in addition to providing trans-tissue abutments, can incorporate integrally posts, post and coping structures, and anchors of various kinds, oriented on the detailed axis.

The general object of invention is to provide parallelism correction to dental implants which are not axially aligned on or parallel to a desired axis in a reliable, precise, and reproducible manner. Other general objects are to provide strong, rigid, corrector structures which in addition to being precise will be rigid and strong, and will not present a risk of failure during use.

The above-described and other objects and features of the invention will be better understood from the following descriptions of certain exemplary embodiments. This description refers to the accompanying drawings, in which;

FIG. 1 schematically illustrates a case in which the invention is useful;

FIG. 2 schematically illustrates preparation of the case for taking an impression;

FIGS. 2-4, inclusive, show further steps in the process of preparing the case for making a parallelism corrector;

Figure 12:
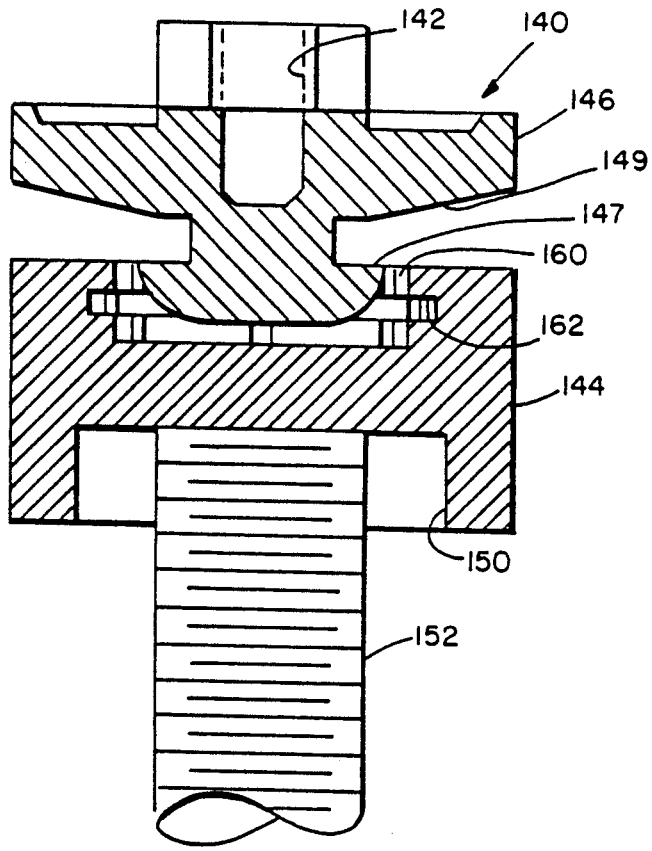
Figure 13:
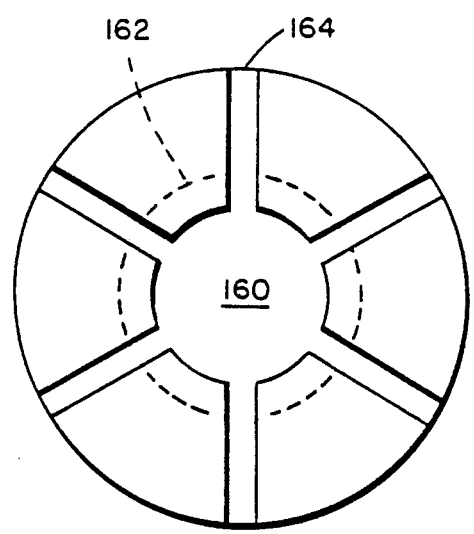
Figure 14:
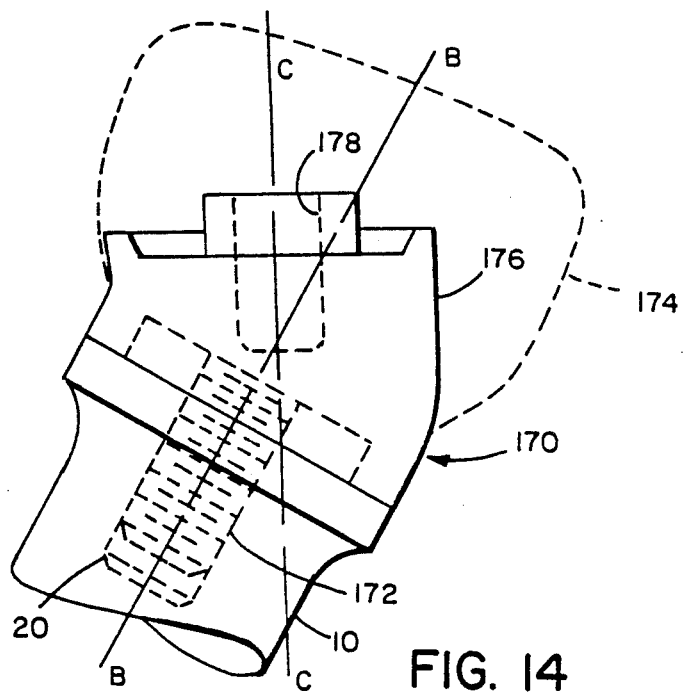

FIGS. 7-11, inclusive, illustrate use of the invention to provide a variety of posts and attachments useful to the dentist and the prosthodontist;

FIGS. 12 and 13 show an axially-short embodiment of the invention approximating the axial length of available trans-tissue abutments; and FIG. 14 shows still another embodiment of the invention.

DESCRIPTION OF EXEMPLARY EMBODIMENTS

Figure 1:
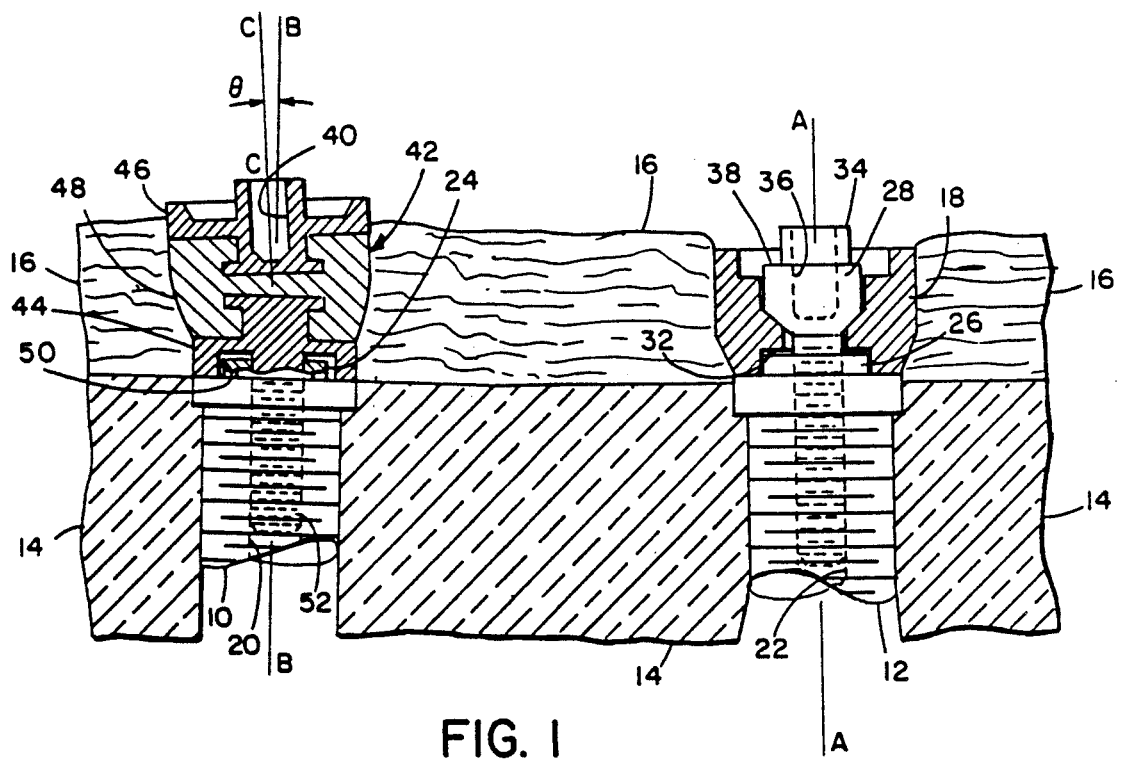

FIG. 1 illustrates a case in which two dental implants 10 and 12, respectively, are installed in a section of jawbone 14 covered with gum tissue 16. The longitudinal axis B-B of the first implant 10 is not parallel with the longitudinal axis A-A of the second implant 12. The surgeon decides that parallelism correction should be applied to the first implant 10.

Each of the illustrated implants is a known commercially available product which has at its top a non-rotational (e.g.: hexagonal) boss 24, 26, respectively, centrally through which an internally threaded bore 20, 22, respectively, opens and extends axially into the implant. The non-rotational bosses 24 and 26 are not used by the embodiments of the invention that are illustrated and described here; the invention is useful whether or not such bosses or the like are present. A known trans-tissue abutment 18 is fitted to the top of the second implant 12, with an abutment screw 28 threaded into the bore 22. The abutment 18 may have at its bottom a hexagonal recess 32 mating with the hexagonal boss 26 so that the abutment will not rotate on the implant 12. The abutment screw 28 has at its head 38 a second non-rotating boss 34 centrally through which a second internally-threaded bore 36 opens and extends axially into the screw head 38. This second bore 36 axially embraces the axis A-A of the implant, and is the receiving bore used to affix a dental prosthesis to the implant. As thus-far illustrated, the arrangement of components shown at the second implant 12 is a known installation.

Before fitting a prosthesis to the first implant 10 the prosthodontist will seek to provide for that implant a receiving bore 40 on an axis C-C which is parallel to the axis A-A of the second implant. For this purpose the invention provides a parallelism corrector device 42, in place of the usual trans-tissue abutment 18 and abutment screw 28, for example. The illustrated parallelism corrector device comprises a prefabricated base member 44, a prefabricated receiving member 46, and between them an after-fabricated body 48 which is affixed to both members, binds them together into a unitary component, and establishes a correction angle θ between the base and receiving members 44 and 46, respectively. Preferably the base member and the receiving member are each prefabricated (e.g.: machined) to respective generic specifications, and the after-fabricated body 48 is formed, or cast to unique specifications, from the same metal, the desirable metal in the present state of the art being titanium or a titanium alloy. The resulting parallelism corrector device is a unitary component.

The base member 44 has at its bottom, generally flat, side a recess 50 and centrally extending from that recess a threaded post 52 which engages in the bore 20 of the first implant 10. The recess 50 is round and larger than the boss 24, so that the recess encloses the boss without restricting the base member from turning around the axis B-B. For use of the invention with a dental implant that does not have a boss 24 or equivalent protrusion, the recess 50 need not be provided. The threads of the bore 20 and post 52 are indexed so that when the base member 44 is fitted to the implant 10 and the post is screwed into the bore the base member will make contact with the implant at the same reproducible angular orientation around the axis B-B of the implant. For example, if each thread is a single-lead thread, the post 52 will start to engage the thread of the bore 20 at only one possible angular orientation around the axis, and the base member 44 will reproduce the same angular orientation around that axis each time it is affixed to the implant. In this instance, indexed threads in the bore and on the post provide the means to affix the base member to the implant with reproducible orientation around the implant axis B-B. The correction angle θ between the base member 44 and the receiving member 46 is established with a procedure that preserves this orientation information.

Figure 2:
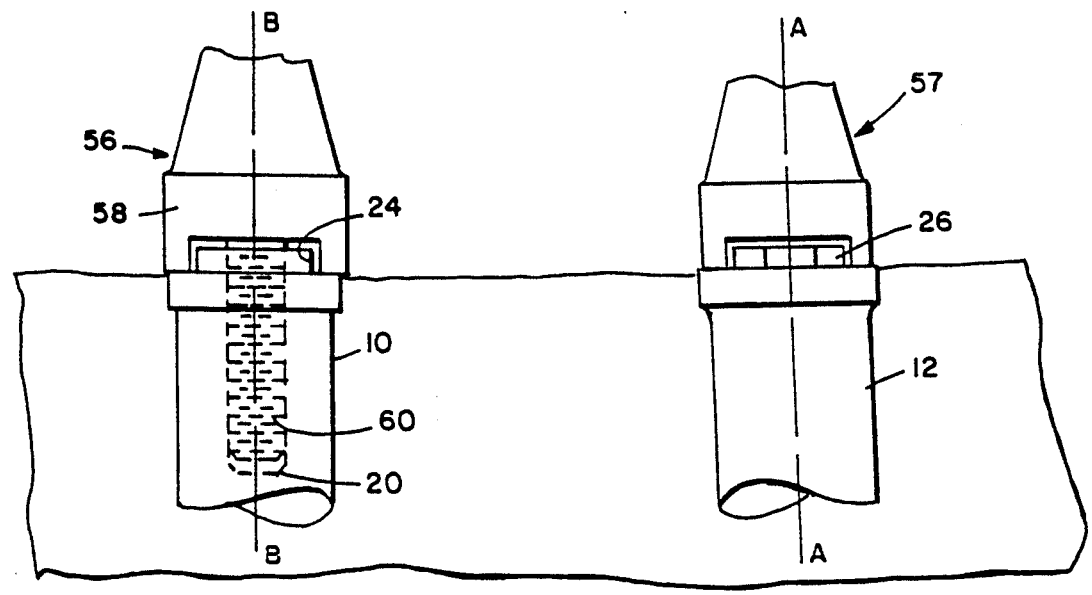
Figure 4:
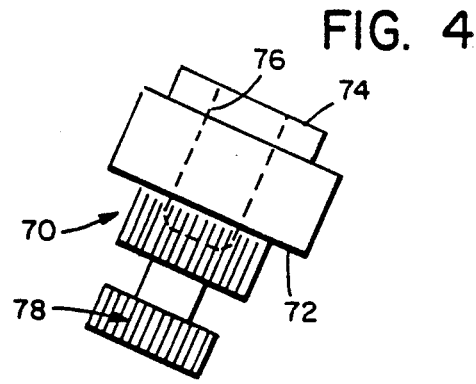

To provide information to a laboratory for making the parallelism corrector device 42 the prosthodontist fits to the first implant 10 a transfer coping 56 which includes a trans-tissue section 58, and a screw-post 60 engageable in the bore 20, illustrated in FIG. 2. Like the screw-post 52 of the base member 44, the screw-post 60 of the transfer coping has an indexed thread which will transfer the orientation information with reference to the axis B-B of the first implant. The significant steps in the subsequent process are apparent from FIGS. 3 to 6, inclusive.

Figure 3:
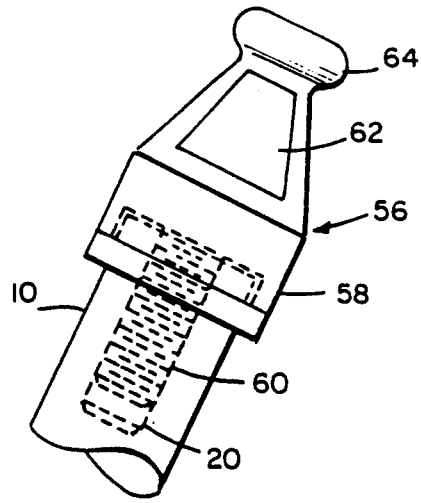
Figure 3A:
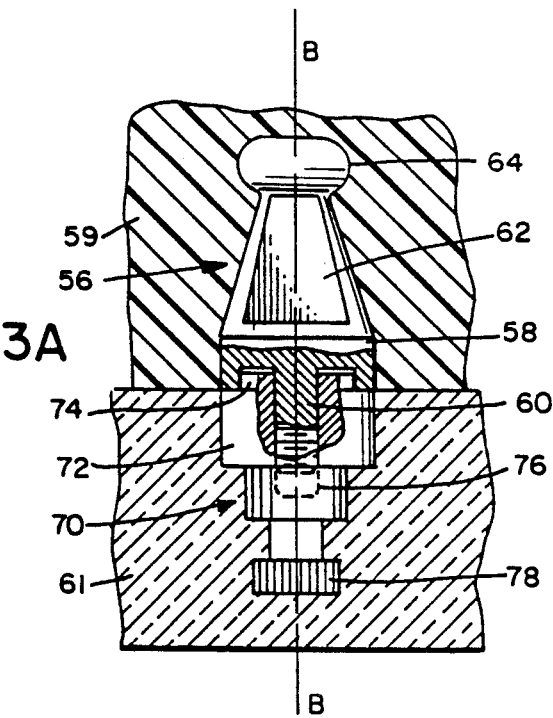

The transfer coping 56 has a flat surface 62, providing a non-circular cross-section at its top portion, and a bulbous boss 64 at its extremity, for retention non-rotationally in the rubber-like (e.g.: hydrocolloid) impression material that is in use for taking dental impressions. A suitable post or coping 57 may be fitted to the second implant, and an impression is made which will transfer the spatial relation and angular difference between axes A-A and B-B, and the orientation of the transfer coping 56 around the axis B-B of the implant 10 to which a parallelism correction is to be applied. Using that impression, one may now make a usual rigid (e.g.: stone) model 61 (FIG. 3A) in which a special implant replica 70, shown in FIG. 4, will be fixed.

The implant replica has a main body 72 with a boss 74 at its top through which a bore 76 opens and extends axially into the body 72. The boss 74 may be round. Alternatively the boss 74 may be omitted. The bore 76 is internally threaded with a thread that is identical to the thread in the bore 20 of the implant 10. After taking the impression 59 and removing it from the patient's mouth, the prosthodontist removes the transfer coping 56 from the implant 10 and installs it in the impression (FIG. 3A), where it takes up the orientation, around its axis B-B, that it had when the impression was made. Alternatively, a laboratory technician can do that step. Then the implant replica is screwed onto the screw-post 60, and comes to rest at the same angular rotation around the screw post 60 as the implant 10. In that manner the implant replica transfers the exact rotational relationship of the coping on the implant to the implant replica. With that information intact, the implant replica 70 is fixed in a rigid modelling material 61 such as casting stone by way of a usual non-rotational retention stem 78, and a rigid model of the jawbone 14 with the two implants 10 and 12 in it is made. This model will, of course, also fix information about the position of the second implant 12 in the jawbone 14, including the direction of its axis A-A (not shown in FIG. 3A).

Figure 5:
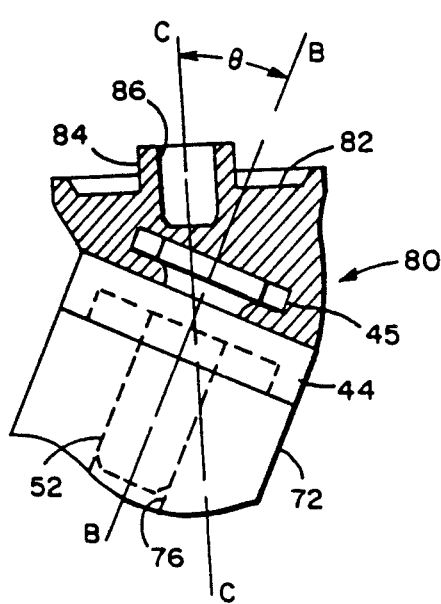
FIG. 5 shows a parallelism corrector according to the invention.

The impression 59 and transfer coping 56 are now separated from the rigid model, and base member 44 is now fitted to the implant replica 70, as is shown in FIG. 5. The base member takes up on the implant replica 70 the exact position around the axis B-B that it will take up when fitted on the implant 10, and its axis coincides with the undesired axis B-B. Using the desired axis A-A as a reference, the laboratory technician can form a corrector member 80. At this juncture, the invention can take one of many possible paths. FIG. 5 illustrates a simple approach, in which a wax-up to form a body 80 oriented to embrace the desired axis C-C is formed on a retention stud 45 which projects from an otherwise generally flat surface of the base member. Using a known investment or lost wax process the body 80 is then cast to the base member 44. If the base member is titanium the body 80 can be cast in titanium, to become an integral part of a trans-tissue direction-changing abutment. Alternatively, the body 80 can be initially larger in size and integral with the base member, and thereafter machined to the unique direction-changing specifications as is described below with reference to FIG. 14. After the body 80 has been formed the top part 82 of it is machined to form a boss 84 and a bore 86 (corresponding to the bore 40 in FIG. 1) which is then internally threaded, if desired.

Figure 6:
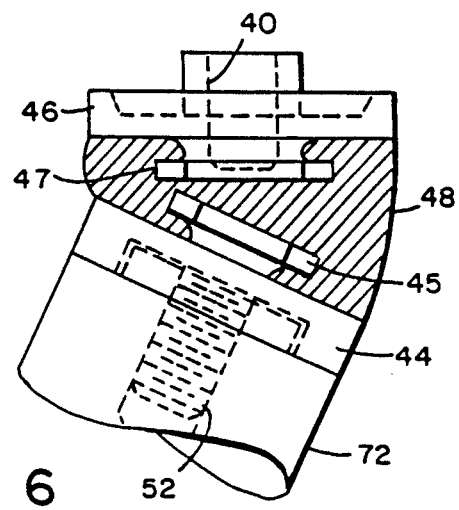
FIG. 6 shows another parallelism corrector according to the invention.

Alternatively, the corrector device 42 shown in FIG. 1 can be made by fitting the prefabricated receiving member 46 to the wax-up (not shown) from which the after-fabricated body 48 is formed (e.g.; of cast titanium). The receiving member 46 has a retention stud 47 projecting from an otherwise generally flat surface embedded in the cast body 48. This is shown in FIG. 6.

FIGS. 7 to 11, inclusive, illustrate, by way of example, respective further alternative structures the invention can provide. Each of these examples is based on a variation of the receiving member 46, using the retention stud 47.

Figure 7:
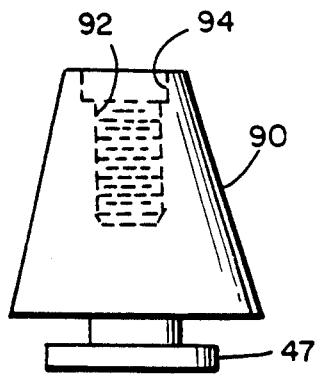
Figure 8:
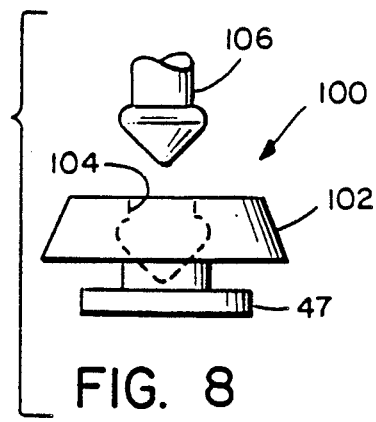
Figure 9:
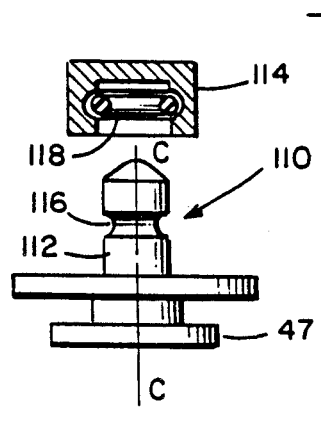

In FIG. 7 a post 90 has at its top an axial bore 92 opening centrally through a recess 94. The invention provides a system which permits removal of a prosthesis and its supporting components from an implant or implants, and to that end this bore may be internally threaded, as shown. FIG. 8 shows a "Zest" anchor 100 in which a main body 102 has an axial bore 104 adapted to receive and retain a stud 106. FIG. 9 shows an "Oso" anchor 110 featuring a post 112 extending on the new axis C-C for receiving a socket member 114. This anchor has an O-ring retainer comprising an annular groove 116 around the post and an O-ring 118 in the socket member. The "Zest" anchor and the "Oso" anchor are known dental devices, useful, for example, to fix full or partial dentures removably in a patient's mouth.

Figure 10:
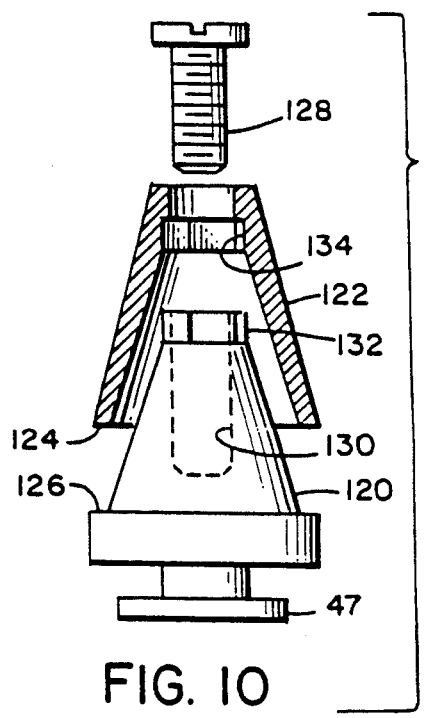

FIG. 10 illustrates an abutment post and a coping which are described and claimed in our co-pending application for U.S. patent Ser. No. 111,868 filed Oct. 23, 1987. An abutment post 120 has the retention stud 47 at its lower end (as seen in the figure) and tapers as it extends supragingivally for reception of a cone-shaped coping 122 which when seated on the post will envelop the tapered portion of the post. In this embodiment of the post and coping combination, the annular bottom edge 124 of the coping meets an annular shoulder 126 of the abutment post when the screw 128 engages in the internally-threaded bore 130 of the post, and fixes the coping on the post. This post has a mount section 132 which mates non-rotationally with a socket section 134 in the coping when the two are fastened together. As is described in our co-pending application, a prosthodontic restoration (not shown) can be fashioned on the coping, and thereby removably fixed on the abutment post.

Figure 11:
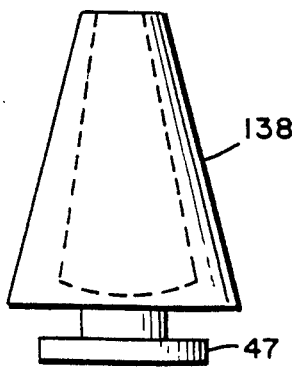

In FIG. 11 is a tapered abutment head post 138 is provided for cemented prosthesis. The invention provides an extensive system of components which can be removably attached to a dental implant, for a wide variety of prosthodontic needs, and which will correct for axial misalignment of a dental implant with a high degree of precision and reproducibility of the correction.

For cosmetic reasons, it is desirable to provide a parallelism corrector which has approximately the same axial length as the trans-tissue abutment 18 (shown in FIG. 1). The parallelism corrector 140 shown in FIGS. 12 and 13 is similar to the corrector device 42 shown in FIG. 1, altered to reduce its axial length. The prefabricated member base 144 has at its bottom side a recess 150 and centrally extending from the bottom surface of that recess a threaded post 152 for engaging in the bore 20 of a dental implant, such as the first implant 10, with the above-described feature of reproducible orientation around the axis B-B. At the top the base member has a re-entrant cavity 160 and a retention groove 162 in the bounding wall of that cavity, to interlock with casting material (not shown). The prefabricated receiving member 146 has a bore 142, and extending from the lower surface 149 a retention stud 147 that is rounded on its lower surface, to extend freedom of the two members 144 and 146 to be fixed on different relative angles. To this end, the lower surface 149 may also be rounded. Casting material (not shown) can be formed between these two members to unite them into a single structure. To permit casting material to flow in the small spaces envisioned in this embodiment, grooves 164 are cut through the walls surrounding the cavity 160, in several places, as is shown in the top plan view of the base member, in FIG. 13.

Dimensional parameters (in inches) of a parallelism corrector device according to FIGS. 12 and 13 may be as follows:

| | |
|---|---|
| diameter of each member 144,146 | 0.176 |
| axial height of base member 144 (excluding post 152) | 0.110 (minimum) |
| axial height of receiving member 146 from bottom of stud 147 to top of bore structure 144 | 0.090 |
| diameter of stud 147 (at maximum) | 0.115 |
| axial height of stud 147 (at maximum) | 0.020 |

| -continued | |
|---|---|
| axial length of stem between stud 147 and surface 149 | 0.020 |
| axial length from crest of surface 149 to top of body 146 (excluding bore structure 141) | 0.030 |

A parallelism corrector as shown in FIG. 5 can be made by casting a corrector member 80 to a base member 44 (or 144), or by machining from a unitary body 170 having the properties of both members, as is illustrated in FIG. 14. This body has a threaded post 172 for engaging in the threaded bore 20 of the first implant 10 with reproducible orientation around the axis B-B of the first implant. This body also has, initially, a mass 174, outlined in dashed-line, which is a rough-machined blank from which a parallelism corrector can be machined using data provided to a machining facility by the prosthodontist doing the restorative surgery. These data are derived from the procedure described above with reference to FIGS. 3, 3A and 4. The surgeon uses the implant impression coping 56 and the implant replica 72 to transfer these data from misaligned implant 10, including the angular orientation of the internal threads in the bore 20, to make a rigid model from the initial impression in resilient material (e.g.: hydrocolloid). This model, with all pertinent data preserved in it, is sent to a machining facility. The machining facility assembles a rough machined abutment blank 170 to the model and marks the blank with reference points for machining. Using facilities that are available to machine shops, the blank 174 is machined to a desired shape and contours 176, and a bore 178 is formed on the desired axis C-C. The finished parallelism-corrected abutment 170 is returned to the surgeon together with the model.

The exemplary case illustrated in FIG. 1 is but one of many situations which may require alignment or parallelism correction for a misaligned dental implant. In a case where a single implant is implanted in a patient who has nearby natural teeth, or a tooth fitted with a root canal post for restoration, the reference axis may be a natural tooth or the root canal post. The invention is applicable to all cases when the axial alignment of a dental implant is sought to be altered in the restoration to be supported on the implant.

We claim:

1. A parallelism corrector device for use with a dental implant that is axially misaligned relative to a desired axis, said corrector device comprising a base member adapted for connection to said implant on its misaligned axis with a prescribed orientation around said misaligned axis, connector means for removably attaching said base member to said implant with said prescribed orientation, a prosthesis-support member having means to support a prosthesis on a support axis that is fixed relative to said support member, each of said base and support members being a solid body spaced from the other and having a surface bearing a non removable interlock element projecting toward but spaced from the other member, and rigid substantially non-bendable joining means formed in the space between said surfaces embracing said interlock elements to fix said members together with an angle between said surfaces such that when said base member is so connected to said implant said support axis coincides substantially with said desired axis.

2. A parallelism corrector according to claim 1 in which said means to fix said members together is a rigid material cast in place between said surfaces.

3. A parallelism corrector according to claim 2 in which said member and said casting material are all made of the same material.

4. A method of providing axial parallelism between a prosthesis to be supported on an axially misaligned dental implant fixed in the jawbone of a person and a reference axis at another position in said jawbone, comprising the steps of fitting to said implant with a prescribed orientation around the axis of said implant a transfer coping which extends coaxially from said implant and has a portion containing means to indicate the angular orientation of said coping around the axis of said implant, making an impression in flexible impression material of said jawbone including said reference axis with said transfer coping in place so as to embrace said angular orientation indicating portion of said transfer coping and thereby to reproduce the spatial relation and angular difference between the axis of said implant and said reference axis together with the angular orientation of said transfer coping around the axis of said implant, transferring said transfer coping from said implant to its location in said impression, fitting to said transfer coping an implant replica which when fitted reproduces the direction of the axis of said implant relative to said reference axis together with the angular orientation of said transfer coping around said axis of said implant, making a rigid model of said jawbone with said implant replica fixed in it representing said implant, fitting to said implant replica a prefabricated base which reproduces on said implant replica the angular orientation of said transfer coping around said axis of said implant, and fabricating on said base while the latter is fitted to said implant replica a corrector member which embraces an axis that is parallel to said reference axis.

* * * * *